United States Patent [19]

Bazenet

[11] Patent Number: 4,729,384

[45] Date of Patent: Mar. 8, 1988

[54] BALLOON ASSEMBLY FOR ESOPHAGEAL PROBE

[75] Inventor: Jean-Pierre Bazenet, Corenc, France

[73] Assignee: Jacques Chevallier, Le Mesnil St. Denis, France

[21] Appl. No.: 882,273

[22] Filed: Jul. 7, 1986

[30] Foreign Application Priority Data

Jul. 8, 1985 [FR] France ................. 85 10768

[51] Int. Cl.⁴ .................. A61B 5/02; A61M 25/00
[52] U.S. Cl. ...................... 128/691; 128/642; 128/772; 604/96; 604/103
[58] Field of Search ............ 128/639, 642, 772-773, 128/419 P, 784, 786, 691; 604/96-103

[56] References Cited

U.S. PATENT DOCUMENTS

| | | | |
|---|---|---|---|
| 3,749,086 | 7/1973 | Kline et al. | 128/772 |
| 4,276,874 | 7/1981 | Wolvek et al. | 604/96 X |
| 4,304,239 | 12/1981 | Perlin | 128/786 X |
| 4,327,709 | 5/1982 | Hanson et al. | 604/96 X |
| 4,545,367 | 10/1985 | Tucci | 604/96 X |
| 4,545,390 | 10/1985 | Leary | 128/772 |
| 4,552,127 | 12/1985 | Schiff | 604/96 X |
| 4,619,274 | 10/1986 | Morrison | 128/772 |

Primary Examiner—Edward M. Coven
Assistant Examiner—Angela D. Sykes
Attorney, Agent, or Firm—Karl F. Ross; Herbert Dubno

[57] ABSTRACT

An intracorporal probe has a flexible and generally nontwistable element having front and rear ends, a flexible and continuous sleeve substantially surrounding and loosely receiving the element between its ends, and a sensor unit mounted on the front end of the element past the sleeve and itself having a front end. Thus twisting of the rear end of the element will twist the sensor unit and will twist the element relative to the sleeve. A forwardly tapered and flexible tip is carried on the front sensor end and a balloon is engaged around the unit between the tip and the sleeve at the front element end. The tip is mainly formed of silicone of a hardness between 50 shore and 100 shore.

12 Claims, 16 Drawing Figures

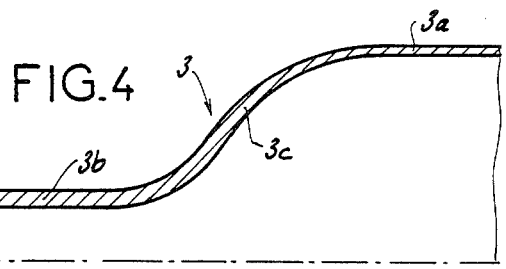
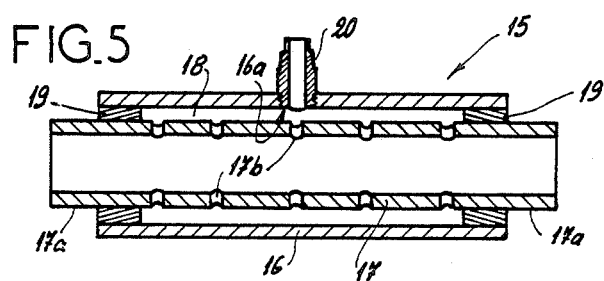
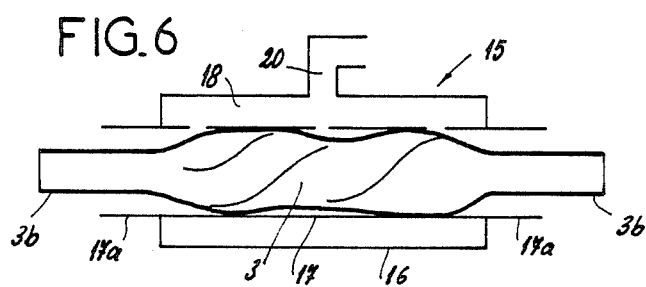
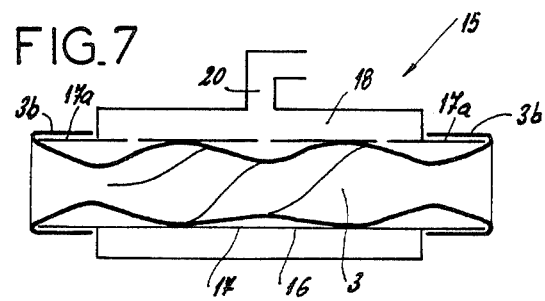

BALLOON ASSEMBLY FOR ESOPHAGEAL PROBE

FIELD OF THE INVENTION

The present invention relates to a probe for use inside the human body. More particularly this invention concerns such a probe used in the esophagus to monitor bodily functions like aortic flow.

BACKGROUND OF THE INVENTION

French patent application No. 78-14,494 and the article "Mesure du debit aortique par echo Doppler et sonde intraoesophagienne" (*Journal Francais d'Echographie*, October 1983) describe a medical procedure whereby one inserts a listening probe into a patient's esophagus to monitor aortic flow. The probe has a flexible tube provided at one end with an inflatable rubber balloon inside of which is provided at least one sensor, typically an ultrasonic transducer. Feed and output cables extend inside the tube from the sensor to the outside. Once inserted to the proper level in the esophagus the probe can be filled up to swell it and cause it to tightly fill the esophagus so as to form a good sound-transmitting connection with the surrounding body structures, in particular the aorta.

In order to orient the sensor so it is facing the right way once the probe is installed, it is carried at one end of a nontwist cable that extends back along the tube and that is attached to operating mechanism so its rear end can be twisted, thereby rotating the sensor carried on its opposite front end inside the balloon. The cable fits somewhat loosely in the tube so that it can rotate fairly freely therein.

Such a setup has several main disadvantages. First of all it is fairly difficult to insert the probe, which typically must enter via the patient's nose as the conditions normally checked with such a probe are only performed on gravely sick patients who already have mouth tubes. The probe end of the assembly is fairly rigid and hard, being formed by the support and the sensor it carries covered by the latex balloon, so such insertion is very difficult and often fairly painful. In addition the unit is fairly complex so that the probe itself is an expensive item to manufacture, entailing molding and electronics technology at high tolerances.

The latex forming the balloon and the tube must be very thin so that it poses minimal interference to the taking of accurate measurements. As a result it is fairly fragile and after some use, normally more than ten times, it is worn out. Similarly, the tube is worn by friction against the cable inside itself. Since the entire assembly is thus rendered useless, the result is that the cost per use of such a probe is very high, as the high cost of manufacture cannot be recovered over a meaningful long service life.

OBJECTS OF THE INVENTION

It is therefore an object of the present invention to provide an improved internal body probe.

Another object is the provision of such an internal body probe, particularly use for esophageal monitoring of aortic flow, which overcomes the above-given disadvantages, that is which is relatively inexpensive to manufacture and durable, and which will have a very long service life.

SUMMARY OF THE INVENTION

An intracorporal probe according to the invention has a flexible and generally nontwistable element having front and rear ends, a flexible and continuous sleeve substantially surrounding and loosely receiving the element between its ends, and a sensor unit mounted on the front end of the element past the sleeve and itself having a front end. Thus twisting of the rear end of the element will twist the sensor unit and will twist the element relative to the sleeve. A forwardly tapered and flexible tip is carried on the front sensor end and a balloon is engaged around the unit between the tip and the sleeve at the front element end. The tip is mainly formed of silicone of a hardness between 50 shore and 100 shore.

Such a probe can be inserted very easily, and the balloon can be a separate replaceable item so even if the balloon is worn out it can be replaced. In one arrangement the balloon and tip are unitary. This allows the entire front covered end to be replaced, and ensures that the relatively soft tip and balloon can easily be fitted to a patient. In this case the tip can have a wholly elastomeric body formed with a rearwardly open recess and can be provided with a nonelastomeric plug fixed thereon and rotationally coupled to the sensor unit.

Normally according to the invention the tip has a forwardly tapered 10%-slope front part of at least frustoconical shape. In any case the tip normally has a wholly elastomeric body formed with a rearwardly open recess and is provided with a nonelastomeric plug fixed thereon and rotationally coupled to the sensor unit. This plug is of metal, is formed with an outwardly open annular groove, and is provided in the groove with an elastomeric ring bonded to the body of the tip. The sensor unit has at its front end a projection carrying a ball that is a snap fit within the plug.

The probe of this invention also has a plug substantially axially blocking the sleeve at the front end of the element and formed with axially throughgoing passages. Thus a liquid can be pumped along the sleeve through the passages into the balloon. The plug has a forwardly tapered front end annularly engaging the sensor unit for very free turning of the sensor and element in the sleeve and plug.

The element itself comprises an inner spring coil, an outer spring coil of opposite hand wound tightly around the inner coil, and another sleeve engaged tightly around the outer coil. In addition the balloon has a center part of large diameter and thin wall thickness and at least one end part of smaller diameter and greater wall thickness, the end part being a tight fit around the front end of the sleeve. According to the invention the center part is of a wall thickness between 0.2 mm and 0.5 mm.

Such a probe is assembled according to this invention by an apparatus comprising a tube extending along an axis and having a center part formed with radially throughgoing perforations, a rearwardly open rear end, and a front end, the rear end of the tube being of greater inside diameter than the largest transverse dimension of the sensor unit and than the normal outside diameter of the rear part of the balloon. Air can be evacuated through the perforations from around a balloon engaged in the tube with its rear balloon end stretched back over the rear tube end. When the balloon and tip are unitary the front end of the tube is closed and complementary to the tip. When the front end of the balloon is like the rear balloon end the front tube end is open like the rear tube end.

Thus the assembly method according to this invention comprises the first fitting the balloon inside the balloon inside the tube with the front and rear parts of the tube juxtaposed with the respective front and rear parts of the balloon and the tubes and balloon centers also juxtaposed. The front end of the tube is then axially closed around the balloon and the rear balloon end is stretched forward over the rear tube end. The space between the balloon and the tube is then evacuated via the perforations until the balloon lies tightly against the inner surface of the tube and the sensor unit is then fitted axially forward through the rear balloon end into the balloon center. The vacuum is relieved and the balloon released to its normal shape. The rear balloon end is then released from the rear tube end engaged elastically around the sleeve at the front element end.

DESCRIPTION OF THE DRAWING

The above and other features and advantages will become more readily apparent from the following, it being understood that any feature described with reference to one embodiment of the invention can be used where possible with any other embodiment. In the accompanying drawing:

FIG. 4 is a large-scale section through a detail of the balloon;

FIG. 5 is a longitudinal and partly diagrammatic section through an apparatus for use with the probe of this invention;

FIGS. 6, 7, 8, and 9 are mainly schematic longitudinal section through the apparatus of FIG. 5 in successive stages of it fitting a balloon over a sensor unit;

SPECIFIC DESCRIPTION

Figure 1:
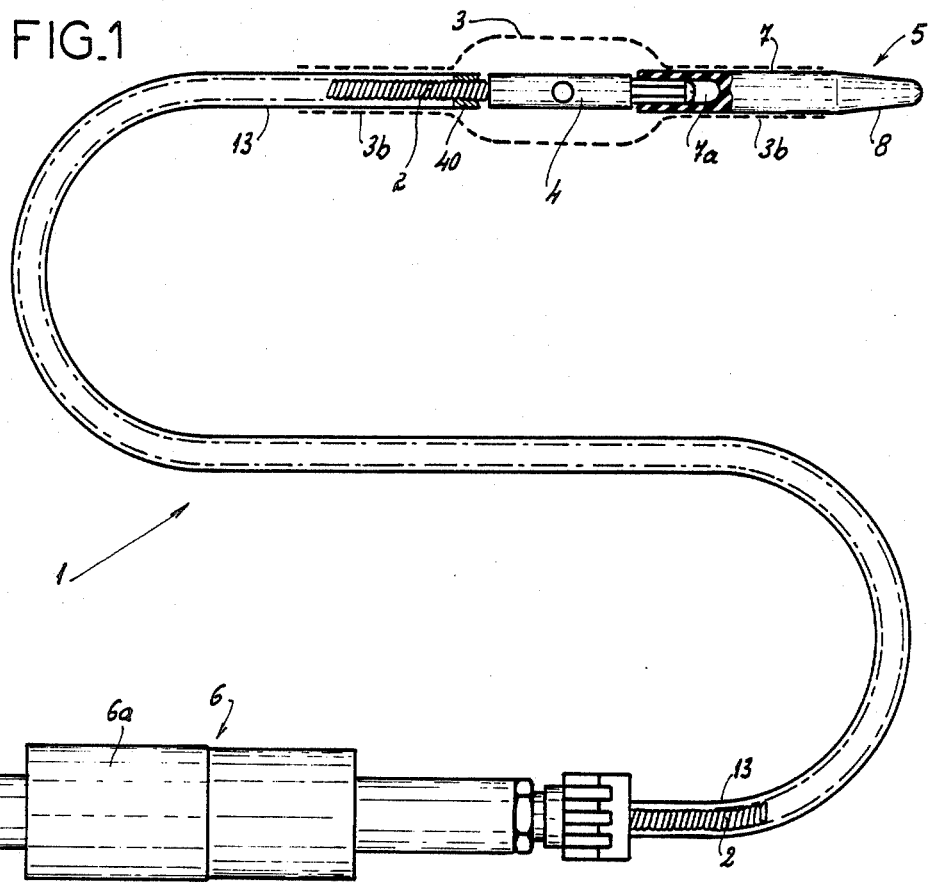
FIG. 1 is a partly sectional side view of the probe according to this invention.

As seen in FIG. 1 a probe 1 according to this invention basically comprises a flexible nontwist tube 2 surrounded by a flexible sleeve 13, the latter normally in vinyl or silicone, and carrying at one end a sensor unit 4 surrounded by a balloon 3, and a tip 5. The opposite tube end is connected to a handle unit 6 having a part 6a that is connected to this tube end to rotate it and thereby also rotate the sensor unit 4. Feed and output cables for sensors in the unit 4 pass longitudinally within the tube 2 and are connected to appropriate power-supply and monitoring equipment. This is the type of probe 1 that can be used for the esophageal monitoring of aortic flow, although the instant invention is not limited to such use.

The tip 5 is formed substantially entirely of a relatively supple material such as latex or silicone having a hardness of between 50 shore and 100 shore. It is centered on an axis A and has a rear cylindrical part 7 and a front frustoconical part 8. The part 8 has a rounded tip and a slope of 10%, that is an apex angle of about 12°. Thus the tip 5 can be relatively easily and comfortably inserted in the patient via the nasal passages.

Figure 10:
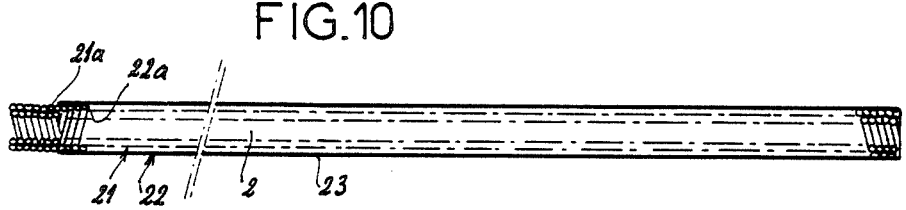
FIG. 10 is a large-scale and partly sectional view of the tube of this invention.

The nontwist tube 2 is shown best in FIG. 10. It has inner and outer spring-wire closed coils 21 and 22 whose turns 21a and 22a are of opposite hand and, for each spring, lie directly against one another. In addition the outer coil 22 is covered with a continuous layer 23 of silicone, either thermoshrunk on it or sprayed on at high temperature. This tube 2 easily accommodates the wires for the sensor unit 4 that is rotationally coupled to it. Thus when the tube 2 is turned, the sensor unit 4 and the delicate feed and supply cable therein will turn identically. Wear will therefore be minimized.

Figure 2:
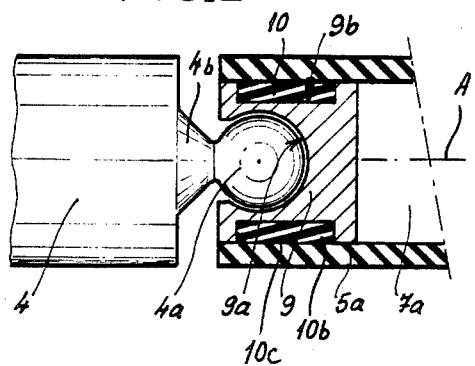
FIG. 2 is a large-scale section through a detail of the probe of FIG. 1.

As seen in FIG. 2 the front end of the sensor unit 4 is formed with a spherical ball 4a attached by a short neck 4b to the unit 4. The rear part 7 of the tip 5 is formed with a centered cylindrical hole 7a that opens backward and receives a generally cylindrical stainless-steel plug 9. This plug 9 is in turn formed with a more than half spherical backwardly open recess 9a into which the ball 4a is a snap fit. This groove 9b receiving a complementarily shaped silicone-rubber ring 10b adhesively secured at the interface 10c to the inside wall of the recess 7a. This type of mounting makes it possible for the tip 5 to rotate about its axis A on the front end of the sensor unit 4 and even to swivel, that is tip so the sensor unit and tip axes are not coaxial, thereon. At the same time the use of a stainless-steel plug 9 with the connection between the like materials of the ring 10 in it and the rear part 7 makes a very solid mounting so that the tip 5 cannot pull off the sensor unit 4.

Figure 3:
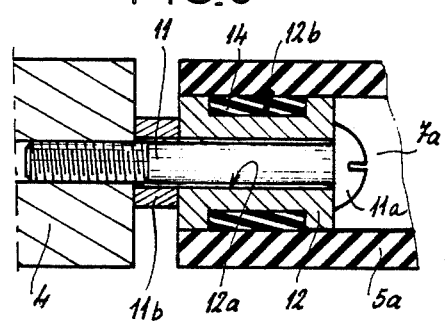
FIG. 3 is a view like FIG. 2 of an alternative tip-mounting system for the instant invention.
Figure 8:
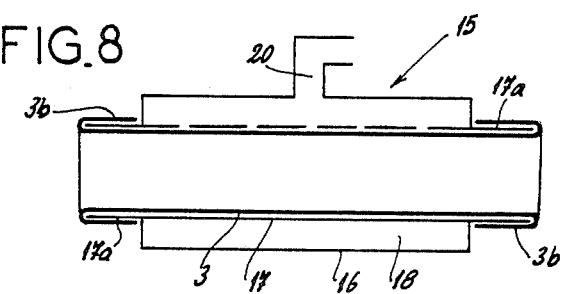

In the arrangement of FIG. 3 the front end of the sensor unit 4 has at its front end a standard slotted screw extending axially forward with its head 11a frontmost. The recess 7a here carries a plug 12 substantially identical to that of FIG. 2 except that it is formed with a central axial bore 12a through which the shank of the pivot screw 11 extends, and a spacer collar 11b is engaged axially between the plug 12 and the sensor unit. The plug 12 is formed with a groove 12b like the groove 9b and housing a ring 14 like the ring 10. This connection is inexpensive, simple to make, quite strong, and furnishes excellent rotational action for the tip 5.

Figure 13:
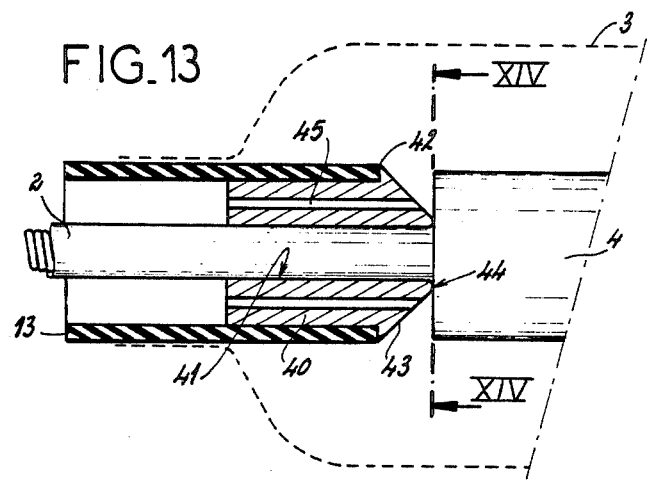
FIG. 13 is a large-scale axial section illustrating the connection of the tube and cable to the balloon and sensor unit.
Figure 14:
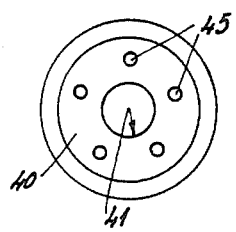
FIG. 14 is an end view as indicated by plane XIV—XIV of FIG. 13.

Another mounting system is shown in FIGS. 13 and 14. Here the end of the sleeve 13 surrounding the tube 2 is fitted with a plug 40 having a central bore 41 through which the tube 2 extends so that this tube 2 can rotate freely in it. The plug 40 is force-fitted into the sleeve 13 and has frustoconically axially forwardly tapered front surface 43 touching the sensor unit at a small annular region 44. In addition this plug 40 is formed with five axially throughgoing holes or passages 45 so that water can be transmitted along the sleeve 13 and through the plug 40 into the balloon 3 indicated in FIG. 13 in dashed lines.

Figure 15:
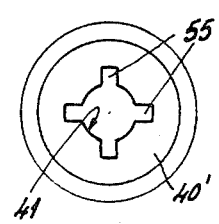
FIGS. 15 and 16 are views like FIG. 14 through two variations on this structure.
Figure 16:
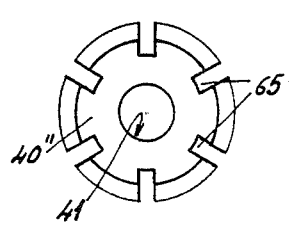

The passages 45 can be of any desired section and instead of the laterally closed passages 45 the bore 41 of a plug 40' can be formed with radially inwardly open and axially throughgoing grooves 55 as shown in FIG. 15. Similarly as shown in FIG. 16 axially throughgoing but radially outwardly open flow grooves 65 can be formed in the plug 40".

As seen in FIG. 4 the balloon 3 is open at both ends and is formed as a central thin-wall sleeve part 3a of large diameter joined to two axially spaced thick-wall sleeve parts 3b of smaller diameter by respective tapered parts 3c of axially outwardly increasing wall thickness but decreasing diameter. The part is normally between 0.2 mm and 0.5 mm thick, preferably 0.3 mm. The parts 3b are relatively somewhat thicker, typically about 0.4 mm when the part 3a is 0.3 mm thick. Such a balloon 3 can be made of a cylindrical tube of constant wall thickness. The smooth transition from the center part 3a to the attachment sleeves 3b, which have an inside diameter that they can fit tightly radially round the rear tip part 7 and front end of the sleeve 13, makes the balloon very durable. The thinness of the center part 3a ensures good transmission of ultrasonic mechanical waves through the balloon 3 to the sensor unit 4 therein. In addition the balloon can be flattened out smoothly during insertion without presenting any particular bumps.

The balloon 3 is fitted to the probe 1 by means of an apparatus 15 shown in detail in FIG. 5. A radially imperforate outer tube 16 coaxially surrounds a somewhat longer but smaller-diameter inner tube 17 whose ends 17a project axially beyond the tube 16 and whose center is formed with radially throughgoing perforations 17b. Spacers 19 block the axial ends of a cylindrical chamber 18 formed between the tubes 16 and 17, which are both of metal. This chamber 18 is open radially inward via the perforations 17b and can be connected to the intake of a pump via a connection 20 extending radially through the outer tube 16.

The apparatus 15 is used to mount a balloon 3 like that of FIG. 4 between the cylindrical part 7 of a tip 5 and the rear end of the tube 2 and sleeve 13. This is done as shown sequentially in FIGS. 6, 7, 8, and 9 by first slipping the flaccid balloon 3 through the apparatus 14 so its sleeve ends 3b project past the inner tube ends 17a, as seen in FIG. 6. Then as seen in FIG. 7 the ends 3b are turned back over the projecting inner-tube ends 17a. This action traps air between the inside of the tube 17 and the outside of the balloon 3.

Figure 9:
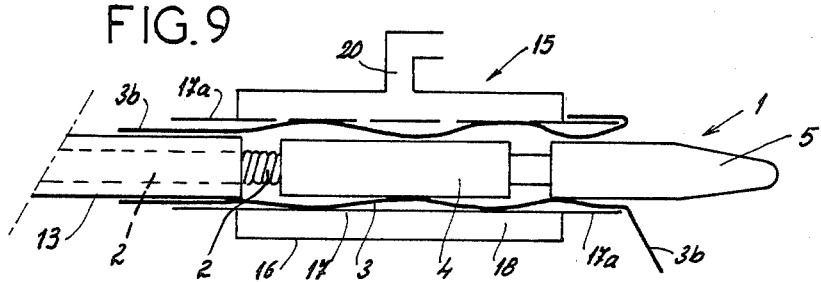

Subsequent pumping out of chamber 18 via the fitting 20 pulls the entire tube 3 out against the inner surface of the tube 17, substantially increasing the inside diameters of the ends 3b without exceeding their elastic limits. The rest of the probe 4 is then pulled through the thus widened tube 3 in the apparatus 15 as seen in FIG. 9. Afterward the vacuum in the chamber 18 can be collapsed and the ends 3b pulled back down to snap tightly over the cylindrical tip part 7 and the front end of the sleeve 130. The elastic fit of these sleeves or cuffs 3b is tight enough that the balloon 3 can be filled with water at slightly superatmospheric pressure, to swell it up to a size sufficient to block it in any normal esophagus, without leaking.

If a balloon 3 needs replacing the old balloon can be removed by the reverse procedure, although cutting it off is warranted if it is no longer usable.

Figure 11:
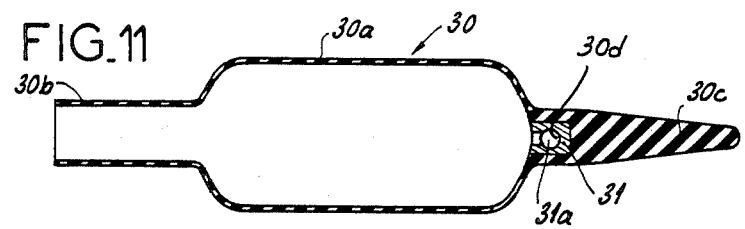
FIG. 11 is a longitudinal section through another balloon and tip according to the invention.

FIG. 11 shows a system according to this invention where a balloon 30 is integrally formed with a tip 30c. The balloon 30 has a large-diameter center part 30a and a rear cuff or sleeve 30b like the parts 3a and 3b, but at its front end is integrally formed with the tip 30c which externally is identical to the tip 5 described above, lacking perhaps the rear cylindrical part 7. A stainless-steel plug 31 received in the rear end of a blind bore 30d in the rear end of the tip 30c is formed with a rearwardly open socket identical to the recess 92 of FIG. 2.

Figure 12:
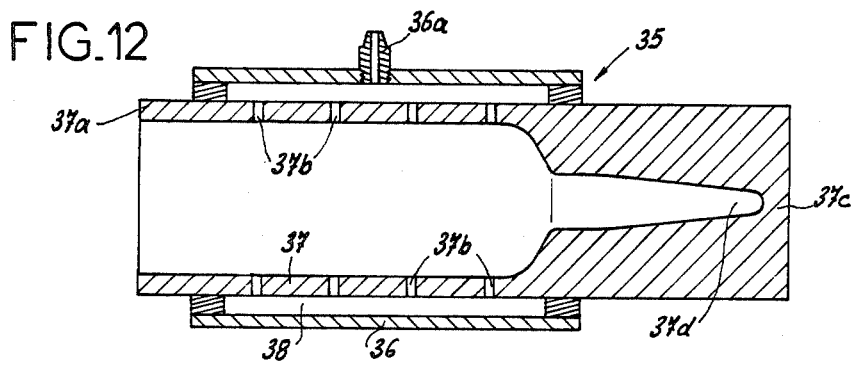
FIG. 12 is a large-scale view of an apparatus for fitting a sensor unit into a balloon.

Such a balloon 30 is fitted to a sensor unit 4 and cable 13 with the apparatus 35 shown in FIG. 12. An outer tube 36 coaxially surrounds an inner tube 37 having a rear projecting end and radially throughgoing bores 37b. In addition this inner tube 37 has an axially forwardly closed end 37c formed with an axially rearwardly open recess 37d complementary to the tip 30c. A fitting 36a opens into the annular passage 38 between the tubes 36 and 37 so that a balloon 30 can have its rear end stretched over the projecting tube end 37a and then be dilated by evacuating the chamber 38, as in FIG. 8.

The plug 31 can have formations on its outer surface to anchor it in the elastomer of the tip 30c and balloon 30. The recess 31a snaps over a ball 4a like that of FIG. 2.

I claim:
1. An intracoporal probe comprising:
a flexible and generally nontwistable element having front and rear ends;
a flexible and continuous sleeve substantially surrounding and loosely receiving the element between its ends;
a sensor unit mounted on the front end of the element past the sleeve and itself having a front end, whereby twisting of the rear end of the element will twist the sensor unit and will twist the element relative to the sleeve;
a forwardly tapered and flexible tip carried on the front sensor end; and
a balloon engaged around the unit between the tip and the sleeve at the front element end, the tip being mainly formed of silicone of a hardness between 50 Shore and 100 Shore, the balloon and tip being unitary, the tip having a wholly elastomeric body formed with a rearwardly open recess and being provided with a nonelastomeric plug fixed thereon and rotationally coupled to the sensor unit.

2. An intracoporal probe comprising:
a flexible and generally nontwistable element having front and rear ends;
a flexible and continuous sleeve substantially surrounding and loosely receiving the element between its ends;
a sensor unit mounted on the front end of the element past the sleeve and itself having a front end, whereby twisting of the rear end of the element will twist the sensor unit and will twist the element relative to the sleeve;
a forwardly tapered and flexible tip carried on the front sensor end; and
a balloon engaged around the unit between the tip and the sleeve at the front element end, the tip having a wholly elastomeric body formed with a rearwardly open recess and being provided with a nonelastomeric plug fixed thereon and rotationally coupled to the sensor unit.

3. The probe defined in claim 2 wherein the plug is of metal, is formed with an outwardly open annular groove, and is provided in the groove with an elastomeric ring bonded to the body of the tip.

4. The probe defined in claim 3 wherein the sensor unit has at its front end a projection carrying a ball that is a snap fit within the plug.

5. An intracoporal probe comprising:

a flexible and generally nontwistable element having front and rear ends;

a flexible and continuous sleeve substantially surrounding and loosely receiving the element between its ends;

a sensor unit mounted on the front end of the element past the sleeve and itself having a front end, whereby twisting of the rear end of the element will twist the sensor unit and will twist the element relative to the sleeve;

a forwardly tapered and flexible tip carried on the front sensor end; and a balloon engaged around the unit between the tip and the sleeve at the front element end, the element having an inner spring coil, an outer spring coil of opposite hand wound tightly around the inner coil over the entire length thereof while the inner coil extends the full length of the outer coil, and another sleeve engaged tightly around the outer coil, said coils each having the successive turns thereof directly in contact with one another.

6. The probe defined in claim 5 wherein the tip is mainly formed of silicone of a hardness between 50 shore and 100 shore.

7. The probe defined in claim 5 wherein the balloon and tip are unitary.

8. The probe defined in claim 5 wherein the tip has a forwardly tapered 10%-slope front part of at least frustoconical shape.

9. The probe defined in claim 5, further comprising
a plug substantially axially blocking the sleeve at the front end of the element and formed with axially throughgoing passages, whereby a liquid can be pumped along the sleeve through the passage into the balloon.

10. The probe defined in claim 9 wherein the plug has a forwardly tapered front and annularly engaging the sensor unit.

11. The probe defined in claim 5 wherein the balloon has a center part of large diameter and thin wall thickness and at least one end part of smaller diameter and greater wall thickness, the end part being a tight fit around the front end of the sleeve.

12. The probe defined in claim 11 wherein the center part is of a wall thickness between 0.2 mm an 0.5 mm.

* * * * *